US006935861B2

(12) United States Patent
Lauciello

(10) Patent No.: US 6,935,861 B2
(45) Date of Patent: Aug. 30, 2005

(54) SETS OF POSTERIOR TEETH

(75) Inventor: Frank R. Lauciello, Elma, NY (US)

(73) Assignee: Ivoclar Vivadent, AG, Schaan (LI)

( * ) Notice: Subject to any disclaimer, the term of this patent is extended or adjusted under 35 U.S.C. 154(b) by 57 days.

(21) Appl. No.: 10/342,411

(22) Filed: Jan. 13, 2003

(65) Prior Publication Data

US 2004/0137407 A1 Jul. 15, 2004

(51) Int. Cl.$^7$ ............................................... A61C 13/08
(52) U.S. Cl. ..................................................... 433/197
(58) Field of Search ................................ 433/196, 197, 433/198, 167, 171, 202.1; 249/54

(56) References Cited

U.S. PATENT DOCUMENTS

| | | |
|---|---|---|
| 1,657,673 A | 1/1928 | Gysi |
| 2,741,845 A | 4/1956 | Appenrodt et al. |
| 3,755,898 A | 9/1973 | Warren |
| 4,194,288 A | 3/1980 | Hass |
| 4,208,794 A | 6/1980 | Gerber |
| 4,226,592 A | 10/1980 | Schreinemakers |
| 4,445,863 A | 5/1984 | Lang et al. |
| 4,795,345 A | 1/1989 | Ai et al. |
| 4,969,817 A | 11/1990 | Hiranuma et al. |
| 4,997,373 A | 3/1991 | Tanaka et al. |
| 5,326,262 A | 7/1994 | Jorgenson |
| 5,501,598 A | 3/1996 | Misch |
| D374,288 S | 10/1996 | Dequeker |
| 5,733,125 A * | 3/1998 | Foser ........................ 433/197 |
| 5,951,289 A | 9/1999 | Kura et al. |
| 6,062,860 A | 5/2000 | Jorgenson |
| 6,273,723 B1 | 8/2001 | Bosshart |
| 6,508,651 B1 * | 1/2003 | Nakamura et al. .......... 433/197 |

OTHER PUBLICATIONS

Lang, B.R. et al, Lingualized Integration: Tooth Molds and an Occlusal Scheme for Edentulous Implant Patients, Implant Dentistry, Fall 1992, pp. 204–211.
Parr, G. R. et al, The Occlusal Spectrum and Complete Dentures, The Compendium of Continuing Education, Jul./Aug. 198?, pp. 241–251, vol. III, No. 4.
Mehringer, E. J., Function of Steep Cusps in Mastication with Complete Dentures, Journal of Prosthetic Dentistry, Oct. 1973, pp. 367–372, vol. 30, No. 4.
Parr, G. R. et al, Lingualized Occlusion—An Occlusion for All Reasons, Dental Clinics of North America, Jan. 1996, pp. 103–112, vol. 40, No. 1.

* cited by examiner

Primary Examiner—Melba Bumgarner
(74) Attorney, Agent, or Firm—John C. Thompson; Alan S. Kooman

(57) ABSTRACT

Sets of posterior teeth which may be used for the production of dentures; the sets including a first set of posterior teeth which provide for lingualized occlusion, and a second set of posterior teeth which provide zero degree monoplane occlusion surfaces. The second set includes maxillary and mandibular premolars and molars, all of the teeth having flat lingual and buccal cusps and a central mesial-distal fossa between the cusps, the central mesial-distal fossa of the mandibular teeth being designed to accommodate the lingual cusps of the maxillary teeth of the first set. The second set has been designed with full length premolars which are of sufficient length to harmonize with canines, the premolars being provided facial surfaces having a cusp like effect by having marginal ridges slightly lower than the center of the buccal and lingual cusps.

9 Claims, 6 Drawing Sheets

SETS OF POSTERIOR TEETH

TECHNICAL FIELD

The present invention relates generally to sets of posterior teeth for dentures, and more particularly to a first set of posterior teeth which provide for lingual contact occlusion, and a second set of posterior teeth which provide for zero degree monoplane occlusion, the upper teeth of the first set being designed for use with the lower teeth of the second set to create another lingual contact occlusion option, and the second set being designed so that they will have a harmonious size and esthetic appearance with the first set.

BACKGROUND OF THE INVENTION

Denture teeth are well known in the art, there being many providers of such teeth. In addition, there are many patents disclosing denture teeth, a few of the U.S. patents being U.S. Pat. Nos. 1,657,673, 2,741,845, 3,755,898, 4,194,288, 4,208,794, 4,226,592, 4,445,863, 4,795,345, 4,969,817, 4,997,373, 5,326,262, 5,501,598, 5,951,289, 6,273,723, and Des. 374,288 to name just a few.

Furthermore, the literature is replete with various recommendations for posterior denture tooth forms primarily based on the functional requirements of mastication and stability of the denture base. The time-honored message has been "the flatter the ridge, the flatter the cusp angles". There seems to be some logic to this statement, as several studies have given this concept some validity by reporting greater denture base distortion during function with steeper cusp angled teeth. Deductive reasoning could conclude that greater denture base movement would result in more soft tissue stress, which would eventually cause accelerated alveolar bone resorption.

In 1941, S. H. Payne, in Volume 47, pp. 20–22 of DENTAL DIGEST, reported on the "modified posterior set-up" of Dr. Edison J. Farmer. This occlusal scheme consisted of prominent maxillary lingual cusps that occluded with relatively flat and uncomplicated mandibular occlusal surfaces. Only the maxillary lingual cusps were in contact with the mandibular teeth. The forces of occlusion were transferred lingual to the mandibular ridge, thus the origin of the term "lingualized occlusion." More recently, the term was changed to "lingual contact occlusion" so that it would not be confused with the suggestion that the teeth are set more lingual to the lower ridge, which can crowd the tongue space. This concept of denture occlusion has gained in acceptance through the years primarily because of its esthetics, biomechanics, simplicity, and favorable patient acceptance. Although the denture tooth debate continues, there does seem to be significant justification for the growing trend toward "lingualized (lingual contact) occlusion". There are many biomechanical, clinical, and technical advantages of this occlusal scheme.

Quite simply put, it has been stated in the literature, "Lingualized (lingual contact) occlusion is an attempt to maintain the esthetic and food-penetration advantages of the anatomic form while maintaining the mechanical freedom of the non-anatomic form".

Traditionally, in order to achieve the lingual contact occlusion concept one would need to mix and match denture teeth from different sets that do not share the same occlusal morphology and facial contours. This may result in the need for excessive tooth modifications. It may also compromise esthetics.

OBJECTS AND SUMMARY OF THE INVENTION

It is an object of the present invention to provide one or more sets of teeth which would overcome the disadvantages of the prior art.

More particularly it is an object of the present invention to provide two sets of posterior teeth which may be used for the production of dentures. Both sets include maxillary and mandibular premolars and molars. Both sets include having progressively longer teeth from the second molar to the first premolar, with the first premolar being the longest so that it harmonizes in length with the typical longer length that is characteristic of canines. The first set of posterior teeth provide for lingualized occlusion. The second set of posterior teeth provide for zero degree monoplane occlusion surfaces with all of the teeth having flat lingual and buccal cusps. The mandibular teeth of the second set have a mesial-distal central fossa which is specifically designed to accommodate the lingual cusps of the maxillary teeth of the first set.

Yet another object of the present invention is to provide the second set of posterior teeth to include having the buccal surfaces of the maxillary premolars giving the illusion of having cusps. This is accomplished by providing the maxillary premolars of the second set with flat buccal and lingual cusps to achieve zero degree monoplane occlusion surfaces and by having the mesial and distal marginal ridges slightly lower than the center of the buccal and lingual cusps. This design is referred to as the "cusp like effect." The term—lower—means closer to the gum line.

The foregoing objects of this invention, as well as other objects and advantages, will become more apparent after a consideration of the following detailed description taken in conjunction with the accompanying drawings in which a preferred form of this invention is illustrated.

DETAILED DESCRIPTION

In General

Figure 1:
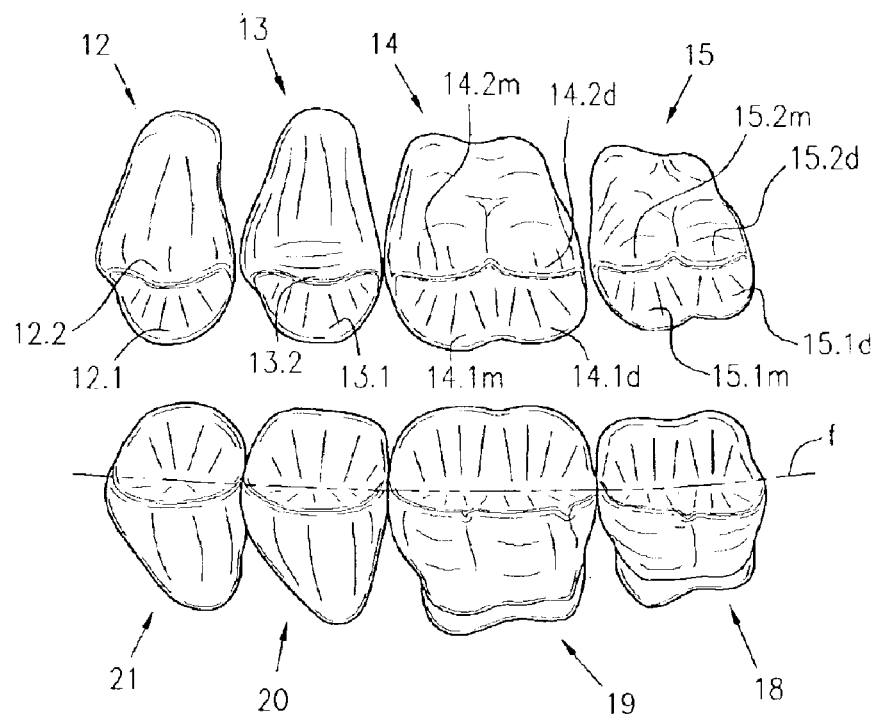
FIG. 1 is a perspective view of upper and lower left side premolars and molars of a first set of posterior teeth of this invention, the teeth being positioned so that occlusal and buccal sides are shown.

As can be seen from the drawings, two sets of posterior teeth are disclosed, which teeth may be used for the production of dentures. The first set shown in FIGS. 1–4 provide for lingualized occlusion, and the second set of posterior teeth shown in FIGS. 5–10 provide for zero degree monoplane occlusion surfaces. The central mesial-distal fossa of the mandibular teeth of the second set, as shown in FIG. 10, is designed to accommodate the lingual cusps of the maxillary teeth of the first set as can best be seen from FIGS. 11 and 12. In addition, the second set shown in FIGS. 5–10 is designed to give the illusion of anatomical teeth.

The First Set of Posterior Teeth

Figure 2:
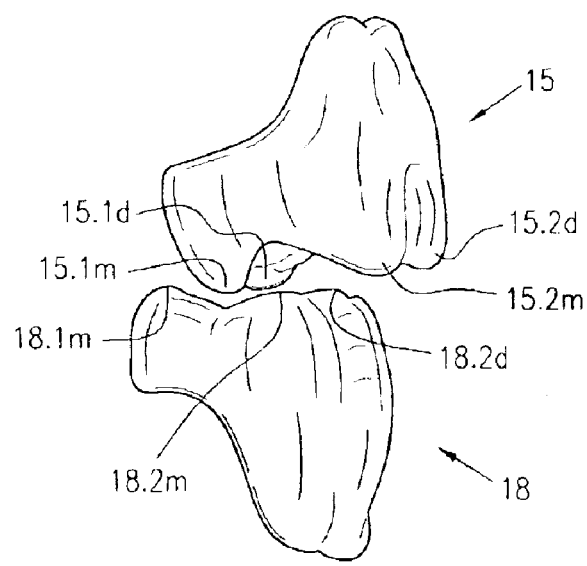
FIG. 2 is a buccal-lingual view of a pair of opposed molars of the first set of posterior teeth of this invention, the teeth being slightly rotated so that both the mesial and distal cusps may be seen.
Figure 3:
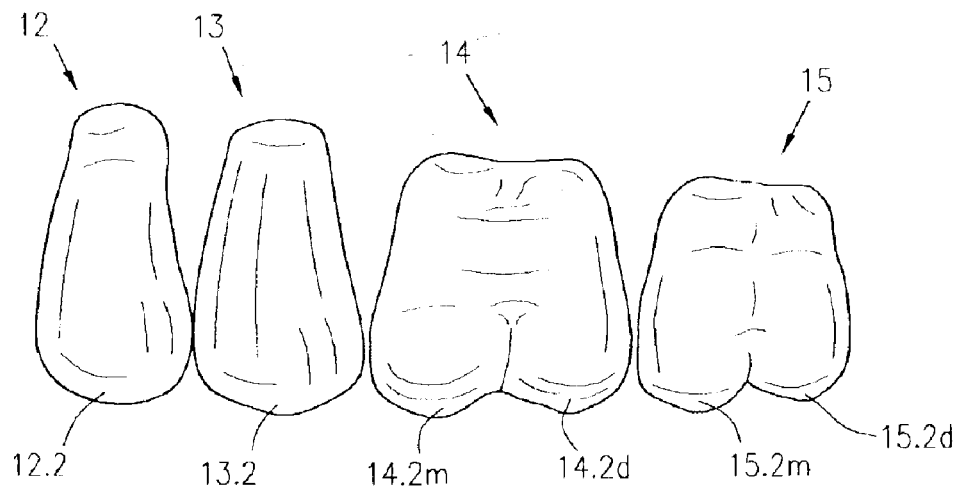
FIG. 3 is a buccal view of the upper teeth of the first set of this invention.

Initially, with reference to FIGS. 1–3, a first set of posterior teeth suitable in the manufacture of dentures is illustrated. This set of dentures is designed for lingual contact occlusion, i.e. wherein only the maxillary lingual cusps contact the mesial-distal central fossa of the mandibular teeth. As this set of teeth is designed for lingual contact, the cusp angles of the lower molars and premolars have buccal cusp angles of 20° and lingual cusp angles of 15°. Thus, the teeth occlude in a manner similar to anatomical teeth, but are designed to have a more forgiving intercuspation.

In FIGS. 1–3 the first set of posterior teeth are shown in their normal position, i.e.—with the maxillary premolars and molars being shown above the mandibular premolars and molars. Thus maxillary teeth for the left side are indicated generally at 12, 13, 14, and 15 (using the American Dental Association Tooth Numbering System) and mandibular teeth for the left side are indicated generally at 21, 20, 19, and 18. Right side teeth are mirror images of the left side teeth.

The maxillary premolars 12 and 13 have one functional lingual cusp, and the maxillary molars 14 and 15 each have two functional lingual cusps to maximize the number of penetrating cusp tips. This is especially important if one molar must be eliminated from the set-up, which is often the situation due to lack of sufficient posterior space.

Each of the maxillary premolars 12 and 13 have one buccal cusp 12.2 and 13.2, respectively. Also, each of the premolars 12 and 13 have one functional lingual cusp 12.1 and 13.1, respectively.

Each of the maxillary molars 14 and 15 has two buccal cusps, and each molar 14 and 15 has two functional lingual cusps. The mesial-buccal cusps of the molars 14 and 15 are indicated as 14.2*m* and 15.2*m*, respectively, and the distal-buccal cusps of the molars 14 and 15 are indicated as 14.2*d* and 15.2*d*, respectively. Similarly, the mesial-lingual cusps of the molars 14 and 15 are indicated as 14.1*m* and 15.1*m*, respectively, and the distal-lingual cusps of the molars 14 and 15 are indicated as 14.1*d* and 15.1*d*, respectively.

As can best be seen from FIG. 2 the lingual cusps of the maxillary teeth, for example 15.1*m* and 15.1*d*, are prominent and have relatively steep cusp angles, preferably in the range of 30° or more. In addition, the mandibular teeth of the first set have a buccal cusp formed with a 20° angle, and the mandibular teeth of the first set have a lingual cusp formed with a 15° angle. As can be seen from FIG. 3, the premolars are of a full length and are designed to harmonize with canines.

The mandibular premolars 21 and 20 are provided with one buccal (21.2 and 20.2) and one lingual cusp (21.1 and 20.1). Each mandibular molar 19 and 18 is provided with one mesial-buccal cusp (19.2*m*, 18.2*m*) and one distal-buccal cusp (19.2*d*, 18.2*d*). Each mandibular molar is further provided with one mesial-lingual cusp (19.1*m*, 18.1*m*) and one distal-lingual cusp (19.1*d*, 18.1*d*). In addition, there is an uncomplicated central mesial-distal fossa extending between the cusps of the mandibular teeth, the fossa being represented by the line "f" in FIG. 1. The fossa is uncomplicated in the sense that it is without mesial-distal marginal and oblique ridges. This central channel or fossa easily accepts the opposing maxillary lingual cusps with minimal set-up. It can also be seen that the mandibular cusp angles are minimal and uncomplicated, although there is sufficient cusp angle for bilateral balanced occlusion. The buccal cusps are slightly steeper to facilitate balancing contacts.

Figure 4:
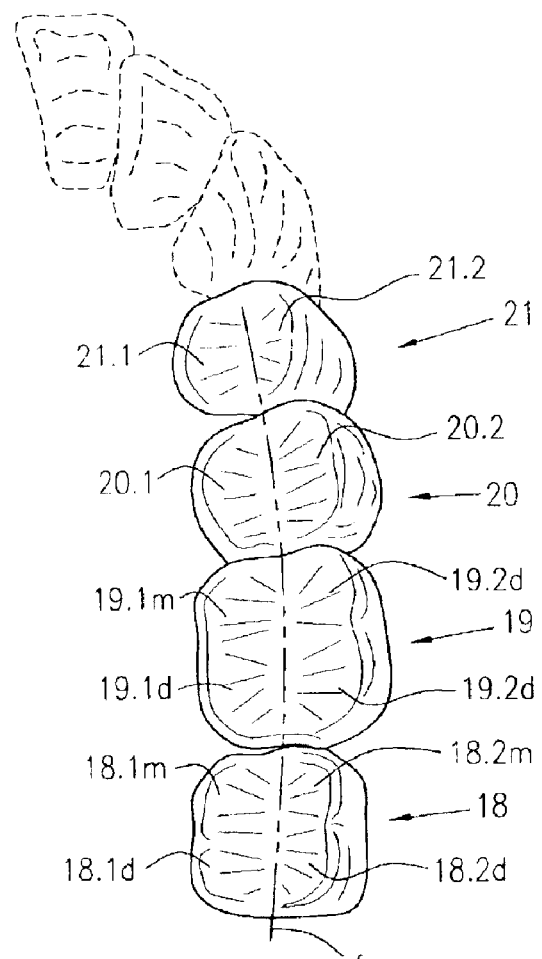
FIG. 4 is a an occlusal view of the mandibular teeth which shows buccal and lingual cusp tips of each denture tooth, which cusp tips are so designed that they may contact a set-up template to stabilize the mandibular teeth during the set-up procedure and greatly facilitate their accurate placement.

In FIG. 4 a further feature of this set of teeth is illustrated. Thus, when positioning the mandibular teeth it is recommended that a set-up template be used. Templates are used to assure that the teeth are aligned evenly from one side to the other. In addition, templates may facilitate the arrangement of anteroposterior (Spee) and mediolateral (Wilson) compensating curves to facilitate bilateral balance. The mandibular teeth of the first set are so designed that the buccal and lingual cusps of each denture tooth contact a set-up template. These contacts stabilize the mandibular denture teeth during the set-up procedure and greatly facilitates their accurate placement.

The Second Set of Posterior Teeth

The second set of posterior teeth are designed to provide zero degree monoplane occlusion surfaces. To this end, the second set includes maxillary and mandibular premolars and molars, all of the teeth having flat lingual and buccal cusps and a central mesial-distal fossa between the cusps. It is a feature of this invention that the central mesial-distal fossa of the mandibular teeth is designed to accommodate the lingual cusps of the maxillary teeth of the first set. To this end, the mesial-distal fossa between the cusps is so designed that it does not have mesial-distal marginal and oblique ridges. A further feature of this invention is that the second set has been designed with full length premolars which are of sufficient length to harmonize with canines, the maxillary premolars being provided facial surfaces having a cusp like effect by having marginal ridges slightly lower than the center of the buccal and lingual cusps, thus having the appearance of natural teeth. As can be seen from FIG. 6 the mesial and distal marginal ridges are slightly lower than the rounded center of the facial surface of the premolars 122 and 113.

With reference now to FIGS. 5–10 parts of the teeth which correspond to the various parts of the teeth in FIGS. 1–4 have been numbered the same plus 100. Thus, the upper premolars and molars of the second set of teeth are numbered 112, 113, 114, and 115, respectively, and the lingual cusps of these teeth are numbered 112.1, 113.1, 114.1*m*, 114.1*d*, 115.1*m*, and 115.1*d*, respectively, teeth 114 and 115 each having mesial and distal lingual cusps. The same numbering system is applied to all components of the teeth which have a correspondence with the first set. As can best be seen from FIGS. 5 and 10, the various cusps are flat, as would be expected from teeth having a zero degree monoplane occlusion surfaces.

Figure 5:
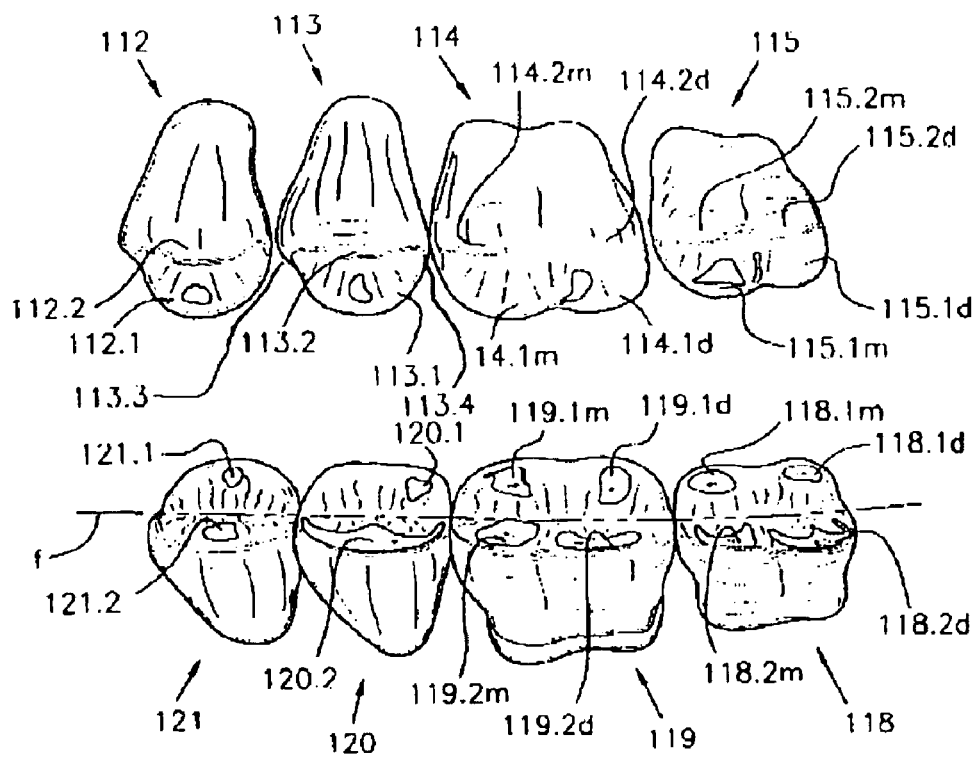
FIG. 5 is a perspective view of upper and lower left side premolars and molars of a second set of posterior teeth of this invention, the teeth being positioned so that the occlusal and buccal sides are shown.
Figure 6:
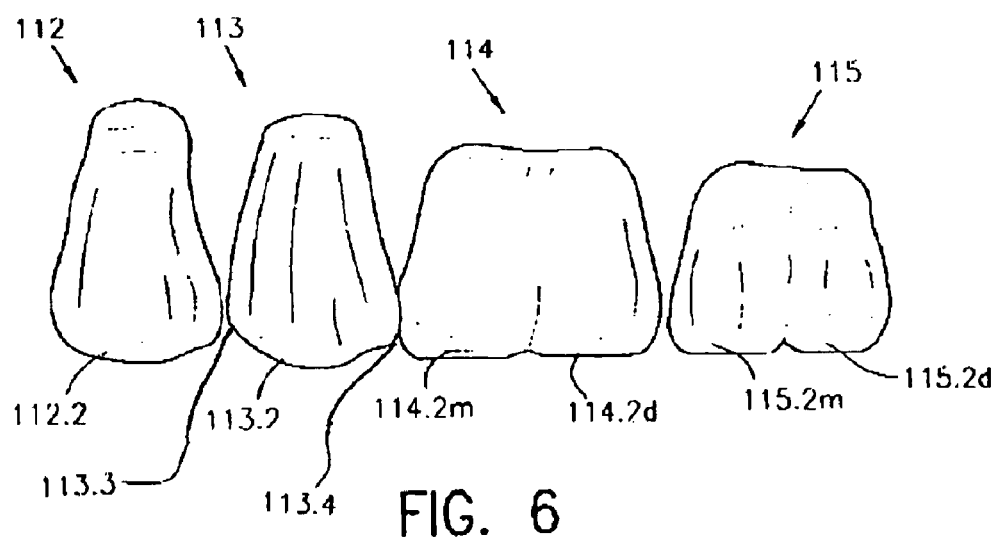
FIG. 6 is a buccal view of the upper teeth of the second set of this invention.
Figure 7:
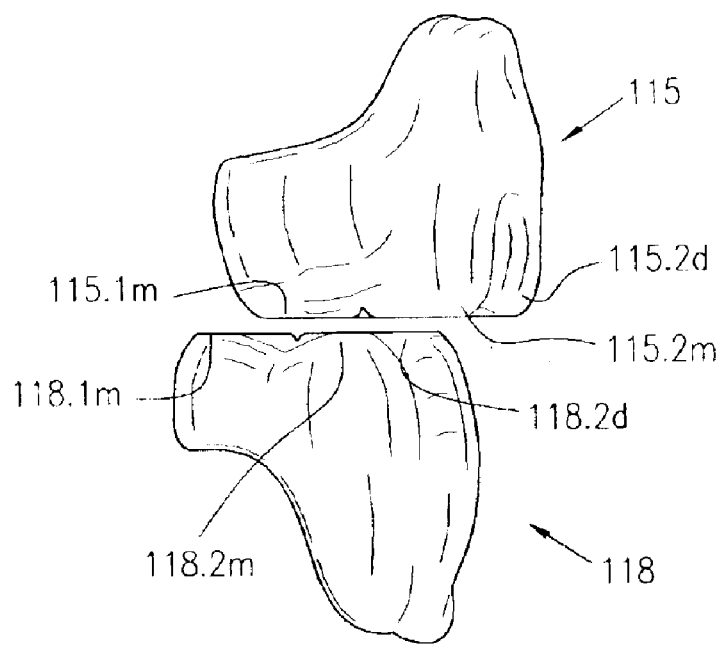
FIG. 7 is a buccal-lingual view of a pair of opposed molars of the second set of posterior teeth of this invention, the teeth being slightly rotated so that both the mesial and distal cusps may be seen.
Figure 8:
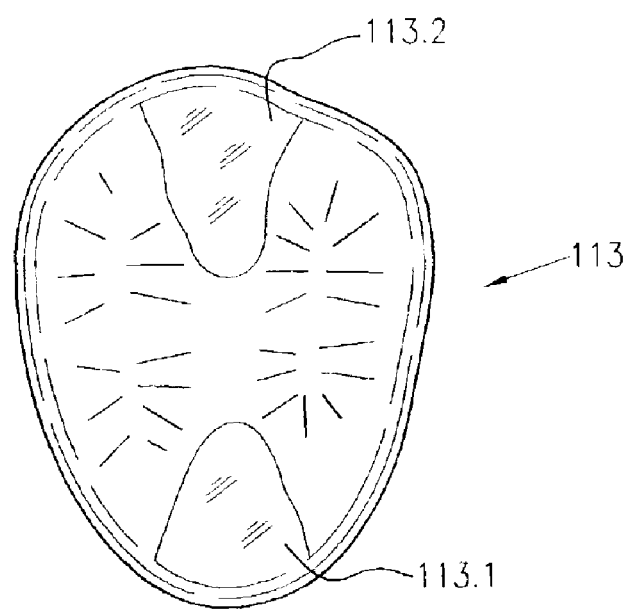
FIG. 8 is an occlusal view of an upper premolar of the second set of this invention.

As previously noted, the maxillary bicuspids 112 and 113 have a cusp like effect, which can best be seen from FIG. 6. This is accomplished by having the mesial and distal marginal ridges slightly lower than the center of the buccal and lingual cusps. Thus, with reference to premolar 113 as shown in FIGS. 5, 6, and 9, it can be seen that the mesial and distal marginal ridges 113.3 and 113.4 are lower than the cusps 113.1 and 113.2, and are lower than the facial or buccal surface of the premolar 113.

Figure 9:
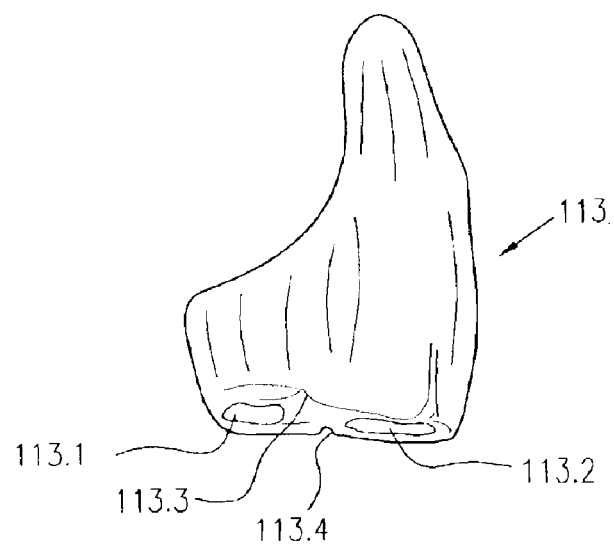
FIG. 9 is a side view of an upper premolar showing the marginal ridge at the lower level and buccal and lingual cusps.
Figure 10:
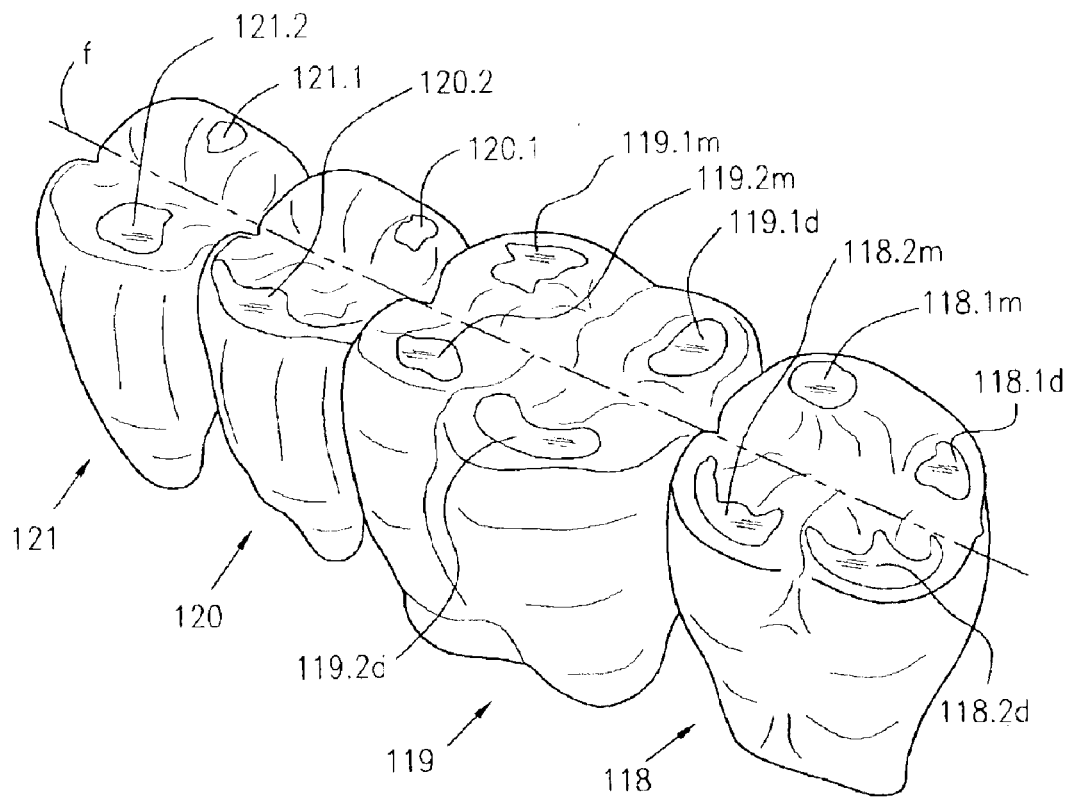
FIG. 10 is a further perspective view of the lower teeth of the second set, to show a mesial-distal central groove which easily accepts the opposing maxillary lingual cusps.
Figure 11:
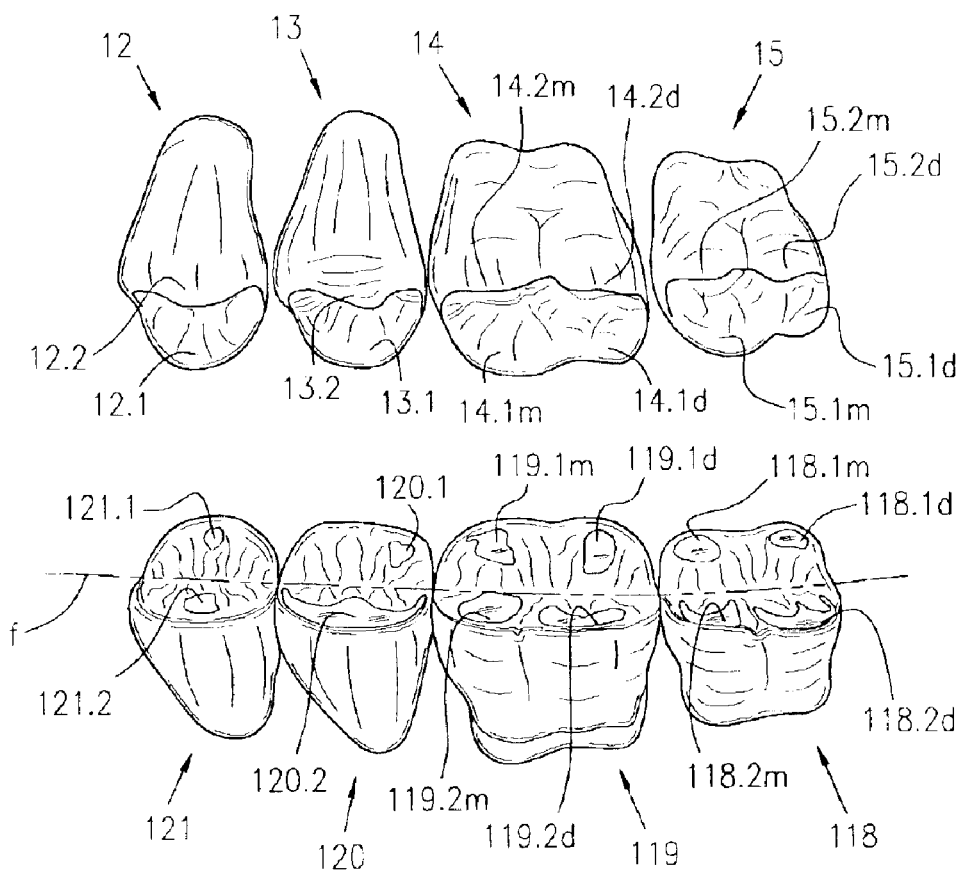
FIG. 11 is a view similar to FIG. 10 but further showing how the lower teeth of the second set may accept opposing maxillary lingual cusps of the first set.
Figure 12:
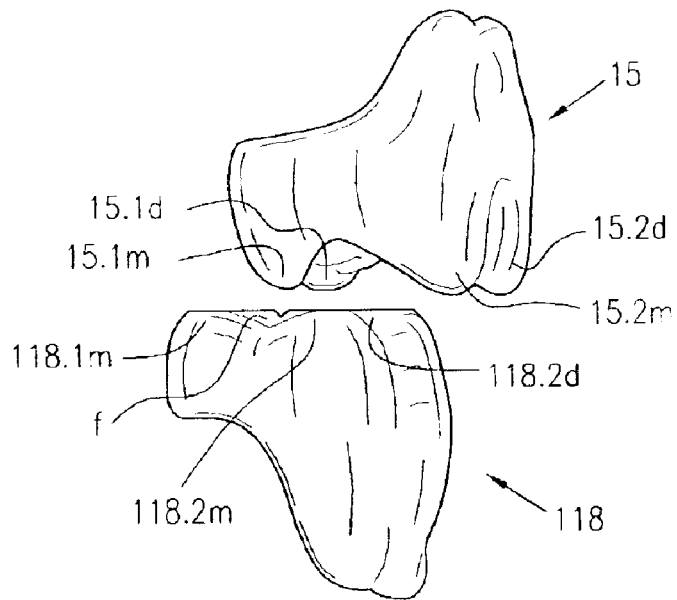
FIG. 12 is a buccal-lingual view of the molars of the teeth shown in FIG. 11.

The Combination of Upper Teeth from the First Set and Lower Teeth from the Second Set With reference now to FIGS. 9 and 10, it is a feature of this invention that the upper or maxillary teeth of the first set are designed for use with the lower or mandibular teeth of the second set to create another lingual contact occlusion option, and the second set being designed so that they will have a harmonious size and esthetic appearance with the first set. This feature is shown in FIGS. 11 and 12. Thus, in FIG. 11, the maxillary teeth of the first set are shown above the mandibular teeth of the second set. It can be seen that they have a harmonious size, and that they match aesthetically. With further reference to FIG. 12, it can be seen that the lingual cusps 15.1m and 15.1d of the maxillary tooth 115 can be easily received in the mesial-distal fossa of the mandibular tooth 118. While only this pair of teeth is illustrated, it is the same for all other upper and lower teeth.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. Sets of posterior teeth which may be used for the production of dentures; said sets comprising:

a first set of posterior teeth which provide for lingualized occlusion, the first set including maxillary premolars and molars and mandibular premolars and molars, all the maxillary premolars and molars and mandibular premolars and molars having lingual and buccal cusps, there being a central mesial-distal fossa between the cusps of the mandibular premolars and molars, the maxillary premolars and molars having prominent lingual cusps with relatively steep cusp angles of 30° or more, and the mandibular premolars and molars having shallow lingual and buccal cusp angles in the range of 15–20°; and a second set of posterior teeth which provide zero degree monoplane occlusion surfaces, the second set including maxillary and mandibular premolars and molars, all of the maxillary and mandibular premolars and molars of the second set having flat lingual and buccal cusps, and a central mesial-distal fossa;

characterized by the central mesial-distal fossa of the mandibular molars and premolars of the second set contact with the corresponding lingual cusps of the maxillary premolars and molars of the first set when in the occlusal position.

2. The sets of posterior teeth as set forth in claim 1 wherein the molars of the first set have two functional lingual cusps to maximize the number of penetrating cusp tips.

3. The sets of posterior teeth as set forth in claim 1 wherein the mandibular premolars and molars of the first set have buccal cusps formed with a slightly steeper angle than the lingual cusps to facilitate balancing contacts.

4. The sets of posterior teeth as set forth in claim 3 wherein the mandibular premolars and molars of the first set have buccal cusps formed with a 20° angle, and the mandibular premolars and molars of the first set have lingual cusps formed with a 15° angle.

5. The sets of posterior teeth as set forth in claim 1 wherein the buccal cusps of the maxillary premolars and molars of the first set progressively decrease in length from mesial to distal teeth.

6. The sets of posterior teeth as set forth in claim 1 wherein the mandibular premolars and molars of the first set are provided with buccal and lingual cusp tips which may contact a template to facilitate the positioning of the mandibular premolars and molars.

7. The sets of posterior teeth as set forth in claim 1 wherein the central mesial-distal fossa of the mandibular premolars and molars of the first set is uncomplicated, that is, without mesial-distal marginal and oblique ridges.

8. The sets of posterior teeth as set forth in claim 1 wherein mesial and distal marginal ridges of the maxillary premolars are slightly lower than the center of the buccal and lingual cusps.

9. A set of posterior teeth which provide zero degree monoplane occlusion surfaces and which may be used for the production of dentures; said set comprising:

maxillary and mandibular first and second premolars and first and second molars which progressively decrease in length from the first premolar to the second molar, and mandibular premolars and molars having flat lingual and buccal cusps, and a central mesial-distal fossa, the central mesial-distal fossa of the mandibular premolars and molars making contact with corresponding lingual cusps of maxillary premolars and molars with lingual cusps which are not flat, when in the occlusal position;

characterized by the maxillary premolars being provided with buccal and lingual cusps having small areas of flatness to provide zero degree monoplane occlusion surfaces, and mesial and distal marginal ridges of the maxillary premolars being slightly lower than the center of the buccal and lingual cusps to provide a cusp like effect.

* * * * *

UNITED STATES PATENT AND TRADEMARK OFFICE
CERTIFICATE OF CORRECTION

PATENT NO.   : 6,935,861 B2  Page 1 of 1
DATED        : August 30, 2005
INVENTOR(S)  : Frank R. Lauciello It is certified that error appears in the above-identified patent and that said Letters Patent is hereby corrected as shown below:

<u>Column 6,</u>
Line 7, -- making -- should be inserted after "set".

Signed and Sealed this

Thirteenth Day of December, 2005

JON W. DUDAS
*Director of the United States Patent and Trademark Office*